US008017016B2

(12) United States Patent
Sims et al.

(10) Patent No.: US 8,017,016 B2
(45) Date of Patent: Sep. 13, 2011

(54) METHOD AND APPARATUS FOR PERVAPORATION CONTROL IN CHROMATOGRAPHIC SYSTEMS

(76) Inventors: Carl W. Sims, St. Paul, MN (US);
Jonathan Thompson, Center City, MN (US); Yuri Gerner, Mendota Heights, MN (US)

(*) Notice: Subject to any disclaimer, the term of this patent is extended or adjusted under 35 U.S.C. 154(b) by 1019 days.

(21) Appl. No.: 11/482,369

(22) Filed: Jul. 7, 2006

(65) Prior Publication Data
US 2008/0006578 A1    Jan. 10, 2008

(51) Int. Cl.
*B01D 15/00* (2006.01)
*C02F 1/44* (2006.01)

(52) U.S. Cl. ........... 210/640; 95/46; 96/6; 210/650; 210/103; 700/273

(58) Field of Classification Search .............. 210/641, 210/649–654, 321.89, 634, 640, 644, 195.2, 210/321.6, 321.72, 321.78, 321.79, 321.8, 210/321.87, 321.88; 95/8, 14–15, 18–19, 95/45–46, 241, 266, 284; 96/4, 6, 10, 101–103, 96/155–156, 173–174, 193, 219, 417, 420–421, 96/424; 700/271, 273; 702/31, 140, 138
See application file for complete search history.

(56) References Cited

U.S. PATENT DOCUMENTS

| 5,013,436 | A |   | 5/1991  | Lee et al. |         |
|-----------|---|---|---------|-----------------|---------|
| 5,139,677 | A |   | 8/1992  | Pasternak       |         |
| 5,160,046 | A |   | 11/1992 | Pasternak       |         |
| 5,173,189 | A |   | 12/1992 | Hoshi et al.    |         |
| 5,266,206 | A | * | 11/1993 | Baker et al.    | 210/640 |
| 5,298,669 | A |   | 3/1994  | Healy et al.    |         |
| 5,448,062 | A | * | 9/1995  | Cooks et al.    | 250/288 |
| 5,538,640 | A | * | 7/1996  | Wijmans et al.  | 210/640 |
| 5,554,286 | A |   | 9/1996  | Okamoto et al.  |         |
| 5,670,051 | A |   | 9/1997  | Pinnau et al.   |         |
| 5,711,882 | A | * | 1/1998  | Hofmann et al.  | 210/640 |
| 6,017,439 | A |   | 1/2000  | Gannon          |         |
| 6,113,797 | A | * | 9/2000  | Al-Samadi       | 210/652 |
| 6,248,157 | B1|   | 6/2001  | Sims et al.     |         |
| 6,440,309 | B1|   | 8/2002  | Cohen           |         |
| 6,494,938 | B2|   | 12/2002 | Sims et al.     |         |
| 6,838,002 | B2|   | 1/2005  | Zeiher et al.   |         |

FOREIGN PATENT DOCUMENTS
EP        0 423 949        4/1991
* cited by examiner

*Primary Examiner* — Tony G Soohoo
*Assistant Examiner* — David C Mellon
(74) *Attorney, Agent, or Firm* — Haugen Law Firm PLLP

(57) ABSTRACT

A method for controlling pervaporation through a membrane includes assessing the vapor pressure of each component material of a mobile phase disposed on a retentate side of the membrane, and maintaining a designed environment on a permeate side of the membrane. The environment maintained on the permeate side of the membrane contains partial pressures of selected component materials of the mobile phase at a level substantially equal to or greater than the respective vapor pressures thereof.

4 Claims, 3 Drawing Sheets

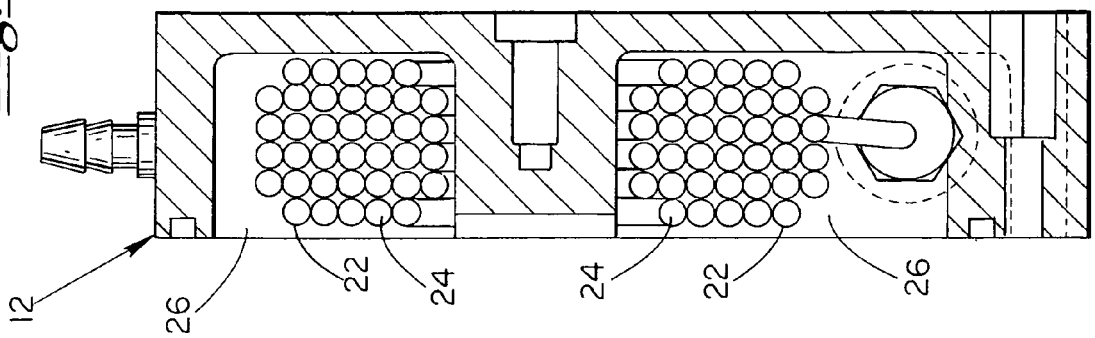
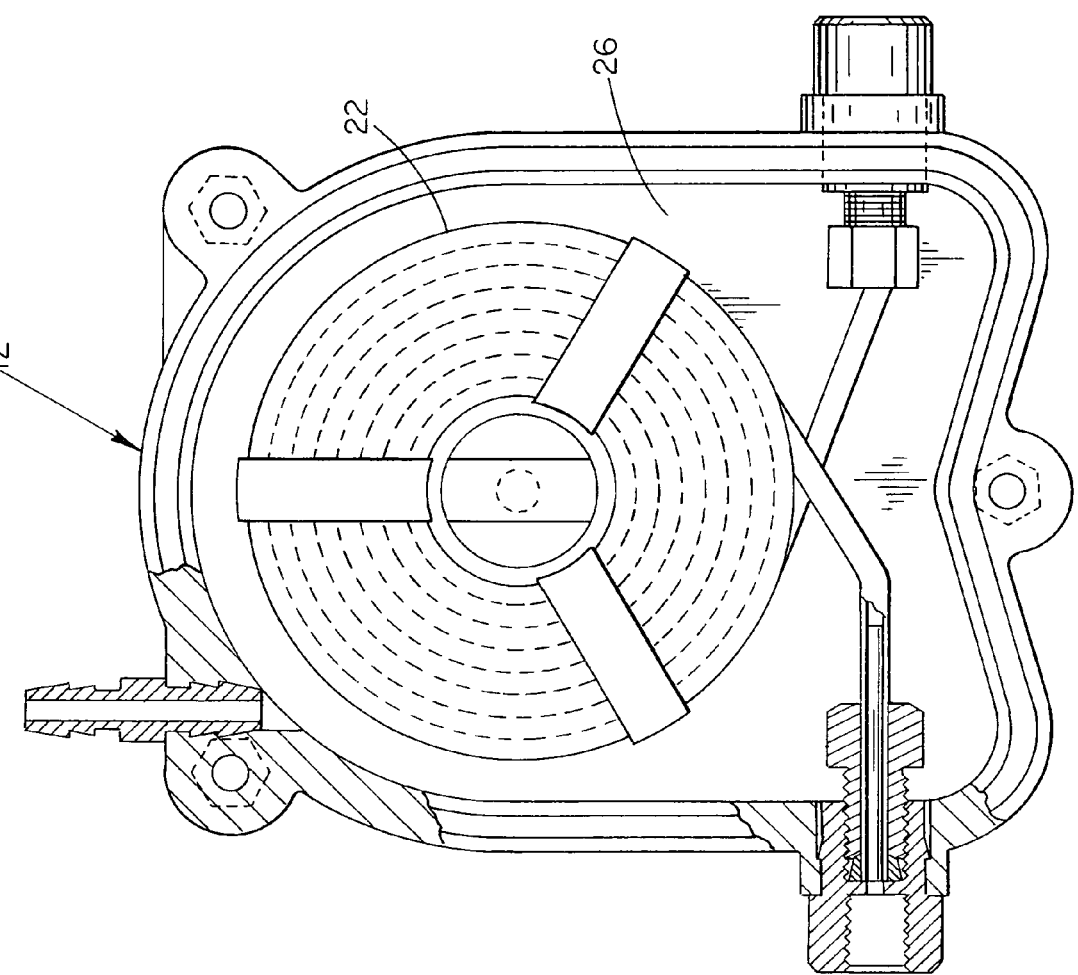

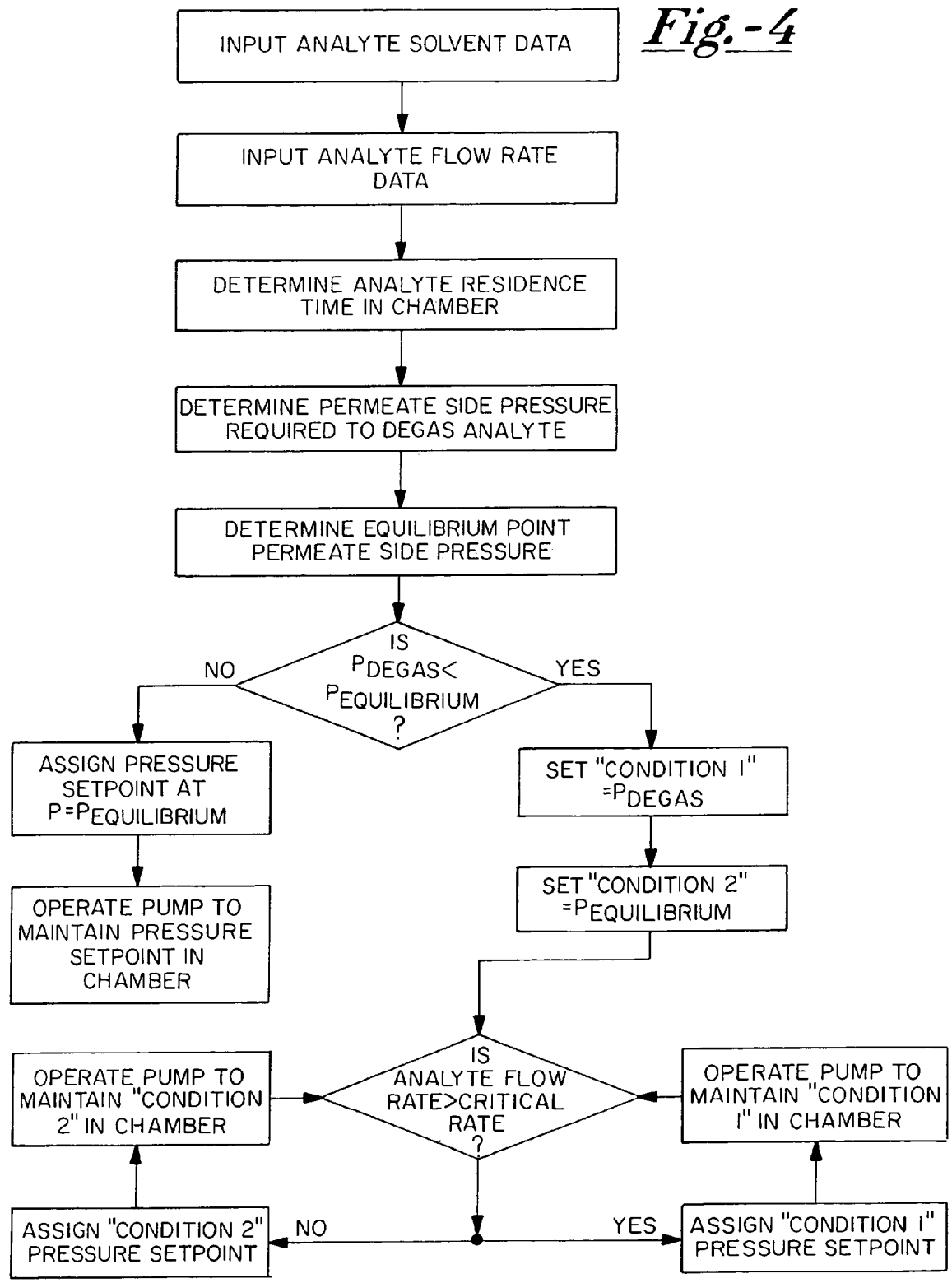

METHOD AND APPARATUS FOR PERVAPORATION CONTROL IN CHROMATOGRAPHIC SYSTEMS

FIELD OF THE INVENTION

The present invention relates to solvent pervaporation generally, and more particularly to control of mobile phase pervaporation in degassing systems utilized in, for example, liquid chromatography applications.

BACKGROUND OF THE INVENTION

Solvent pervaporation through a membrane is a well known phenomenon that has been harnessed in membrane separation applications. For example, the prior art is rich with examples of the use of solvent pervaporation through a membrane for the purpose of concentrating relatively low vapor pressure components on a retentate side of the membrane. In addition, distillation operations utilizing pervaporation through a membrane have been performed to selectively recover solvent components on the permeate side of the membrane.

While the beneficial aspects of pervaporation have long been known and utilized in purposeful solvent separation processes, such pervaporation characteristics can have significant negative effects in mixed-solvent applications wherein the relative concentrations of the respective solvents is desired to be known and/or constant. A particular example of such a mixed-solvent application is in liquid chromatography systems, wherein mobile phases made up of more than one solvent are used. It has been recognized by the Applicants, however, that changes to the relative concentrations of the mobile phases can occur over time, thereby negatively effecting the accuracy of chromatographic analysis.

Pervaporation effects are particularly damaging to analytical accuracy in chromatographic systems utilizing relatively low through-put mobile phase volumes, or in instances wherein the chromatographic instrumentation is only periodically operated without complete flushing of supply lines between each operation. For example, systems that utilize mobile phase flow rates of on the order of nanoliters or microliters per hour are at risk of having the relative concentrations of the solvents making up the mobile phase being substantially modified during analyte transportation through the chromatographic instrumentation.

In particular, liquid chromatography systems typically employ degassing chambers in which the liquid mobile phase is exposed to a degassing environment through a gas-permeable, liquid-impermeable membrane. Such a degassing environment may be, for example, relatively low absolute pressures maintained by evacuation pumps, or relatively low target material partial pressures in a sweep fluid passed through a permeate side of a degassing chamber. Typically, degassing operations have been arranged and controlled to maximize degassing performance on the mobile phase passing through the degassing chamber. To do so, vacuum pumps were programmed to maintain very low absolute pressures on the permeate side of the membrane, or, in cases of a sweep fluid, the sweep fluid utilized contained little or no concentration of the targeted gas species being withdrawn from the mobile phase. In both cases, a target gas concentration differential has traditionally maintained a relatively high value to drive target gas transfer through the membrane to the permeate side. A result of maintaining such a large target gas concentration differential at all times in the degassing chamber is the causation of pervaporative effects. Specifically, relatively long residence time of mobile phase within the degassing chamber having a permeate side maintained at the conditions described above has the tendency to cause mobile phase component materials having relatively high vapor pressures and high membrane solubility to pervaporate through the membrane, while relatively lower vapor pressure mobile phase component materials have a lower tendency, and thus a lower rate, of pervaporation through the membrane. As a consequence, the mobile phase on the retentate side of the degassing chamber can become concentrated in relatively higher vapor pressure component materials, particularly if such mobile phase has a relatively high residence time within the degassing chamber.

It is therefore a principal object of the present invention to provide a control mechanism for maintaining the environment on the permeate side of a membrane at one or more conditions effective in limiting pervaporation through the membrane of a mobile phase having two or more component materials.

It is another object of the present invention to provide a method for controlling pervaporation of a mobile phase having two or more component materials through a membrane.

It is a further object of the present invention to provide a method and apparatus for maintaining the partial pressures of selected ones of the mobile phase component materials on a permeate side of a separation membrane substantially equal to the respective vapor pressures of the selected mobile phase component materials, with such an environment defining a first condition that is maintained on the permeate side of the chamber only during designated time periods.

SUMMARY OF THE INVENTION

By means of the present invention, mobile phase component pervaporation may be limited and controlled to suit the needs of a particular application. The pervaporation control technique utilizes control software operably coupled to a feedback control system that senses conditions within a membrane degassing chamber in which the mobile phase is disposed. Based on the sensed conditions of a permeate side of the chamber, the control software of the present invention operably adjusts the output of environment-modifying devices such as a vacuum pump or sweep fluid inlet lines, so as to obtain at the permeate side, at least at selected intervals, partial pressure values of selected mobile phase components that are equal to or greater than the corresponding vapor pressures of such mobile phase components.

In a particular embodiment, the method of the present invention for controlling pervaporation through a membrane includes assessing the vapor pressure of each component material of a mobile phase disposed on a retentate side of the membrane, and maintaining a designated environment on a permeate side of the membrane. The environment maintained by the method of the present invention contains partial pressures of selected component materials substantially equal to the respective vapor pressures of such component materials.

In another embodiment, the method involves maintaining a designated environment on a permeate side of a membrane disposed in a liquid degassing apparatus, with the environment having partial pressures of selected component materials of a mobile phase of the liquid degassing apparatus substantially equal to the respective vapor pressures of such component materials.

A still further embodiment of the invention involves controlling mobile phase pervaporation in a liquid degassing system by providing a membrane disposed in a chamber such that the membrane separates the chamber into a retentate side and a permeate side. A control mechanism is also provided for selectively maintaining a designated environment on the permeate side of the chamber. A mobile phase having two or more component materials is directed to the retentate side of the chamber, wherein the control mechanism is operated at selected ones of a least two conditions. A first condition of the control mechanism is programmed to maintain partial pressures on the permeate side of selected ones of the two or more component materials substantially equal to the respective vapor pressures of the selected ones of the two or more component materials.

A second condition of the control mechanism described above is programmed to maintain partial pressures on the permeate side of selected ones of the two or more component materials at a level less than the respective vapor pressures of the selected ones of the two or more component materials.

In preferred embodiments, the control mechanism is operably coupled to a pump that is adapted to evacuate the permeate side of the chamber, and wherein the conditions are established by maintaining an appropriate total pressure within the permeate side of the chamber. Example pump operating mechanisms useful in the present invention include those described in U.S. Pat. Nos. 6,494,938 and 6,248,157, which are herein incorporated by reference. The appropriate total pressure for the first condition is about equal to or greater than a sum of the vapor pressures of the selected ones of the two or more component materials, while the appropriate total pressure for the second condition is less than such a sum.

BRIEF DESCRIPTION OF THE DRAWINGS

FIG. 2 is a cross-sectional side view of a portion of the system illustrated in FIG. 1;

FIG. 3 is a cross-sectional end view of the portion of the system illustrated in FIG. 2;

FIG. 4 is a flow diagram illustrating a pervaporation control method of the present invention.

DETAILED DESCRIPTION OF THE PREFERRED EMBODIMENTS

Figure 1:
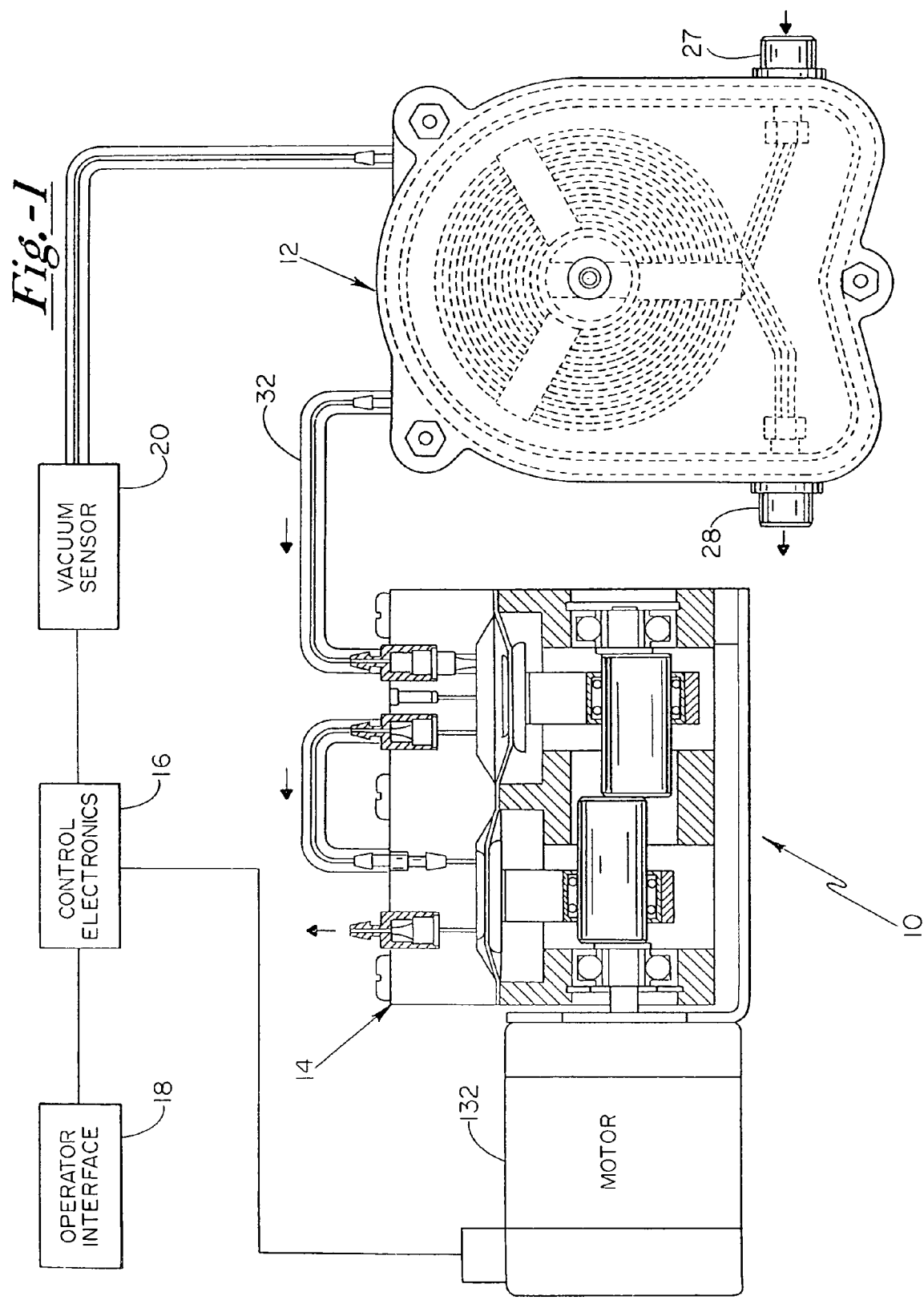
FIG. 1 is a schematic view of a pervaporation control system of the present invention.

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

With reference now to the drawing figures, and first to FIG. 1, a pervaporation control system 10 includes a chamber 12, a vacuum pump 14 and a vacuum sensor 20 operably coupled to chamber 12. Pervaporation control system 10 preferably further includes a control mechanism 16 that is operably coupled to vacuum pump 14 and vacuum sensor 20 so as to selectively maintain a designated environment at portions of chamber 12. An operator interface 18 is also preferably incorporated with pervaporation control system 10, such that an operator may communicate with, and program control mechanism 16.

Chamber 12 may be fabricated from a non-porous, non-absorptive material such as polyphenylene sulfide, PEEK, non-porous metal, or non-porous glass. Such materials inhibit solvent pervaporation through an exterior wall thereof. In addition, transfer tubing 32 between chamber 12 and vacuum pump 14 is also preferably fabricated from a relatively low gas-permeability material, such as PTFE vacuum tubing. The materials making up the containment for the permeate environment are accordingly substantially gas-impermeable.

In the embodiment illustrated in FIGS. 1-3, chamber 12 is a vacuum chamber containing a membrane 22 in the form of a continuous tube that extends between inlet and outlet connections 27, 28 of chamber 12. Membrane 22, however, may be disposed in chamber 12 in a variety of configurations, and being limited only by the requirement that membrane 22 effectively contain the liquid portion of a mobile phase entering chamber 12 at inlet connection 27 on a retentate side thereof. Accordingly, membrane 22 is preferably fabricated from a gas-permeable, liquid-impermeable material. In preferred embodiments, membrane 22 may be extruded from a polymeric resin available from E.I. du Pont de Nemours and Company under the trade name Teflon AF®. Applicants have found that the Teflon AF® represents a good example of a semi-permeable membrane material useful in system 10 of the present invention. Further description of the embodiment illustrated in FIGS. 1-3 is found in U.S. Pat. No. 6,248,157 which is incorporated herein by reference.

As illustrated in FIGS. 2 and 3, membrane 22 divides chamber 12 into a retentate side 24 and a permeate side 26. Liquid mobile phase is preferably directed to retentate side 24 of chamber 12, such that substantially only gaseous/vapor phase species may pass through the wall of membrane 22 to permeate side 26.

Applicants have discovered that the operational control of the environment at permeate side 26 of chamber 12 can limit the extent of mobile phase solvent pervaporation through membrane 22. In particular, maintaining the environment of permeate side 26 at a total pressure reflective of the combined vapor pressures of each mobile phase component material, an "equilibrium point" is developed at which pervaporation of any mobile phase component material substantially ceases. As such, the pressure at permeate side 26 may be controlled to allow only that much mobile phase component material pervaporation to fill permeate side 26 of chamber 12 to a component partial pressure equal to its vapor pressure. In order to limit pervaporation of the mobile phase component material, therefore, total pressure at permeate side 26 is preferably set at the combined vapor pressures of each mobile phase component material. Since such a condition also limits the extent to which the mobile phase may be degassed, a desired aspect of the present invention is to maintain the environment of permeate side 26 at two or more conditions, with at least one condition limiting pervaporation effects, and another condition setting the total pressure at permeate side 26 lower than the respective vapor pressures of the mobile phase component materials to permit rapid degasification of the liquid mobile phase.

With reference to the flow diagram of FIG. 4, control mechanism 16 is preferably programmed to operate vacuum pump 14 via motor 132 to establish a desired vacuum set point at permeate side 26 within chamber 12. As such, control mechanism 16 preferably operates through a feedback control loop of conventional nature, such as through the technique described in U.S. Pat. No. 6,248,157. Information supplied to the feedback control loop utilized by control mechanism 16 of the present invention is generated by vacuum sensor 20, which detects a pressure at permeate side 26 of chamber 12. Such information is utilized by control mechanism 16 to operate vacuum pump 14 at a desired rate so as to maintain a desired pressure set point at permeate side 26 of chamber 12.

To initiate the method of the present invention, a user interacts with operator interface 18 to input known variable values. In particular, the component materials making up the mobile phase are entered, along with a mobile phase flow rate through chamber 12, and physical characteristics of chamber 12. Based on the inputted information, control mechanism 16 determines the mobile phase residence time within chamber 12, and computes a maximum permeate side pressure that still acts to sufficiently degas the mobile phase. Moreover, control mechanism 16 also determines the respective vapor pressures for each component material at the temperature of the mobile phase passing through chamber 12, such that an equilibrium point pressure on permeate side 26 may be calculated.

The pressure set point that is necessary to be established at permeate side 26 in order to operably degas the mobile phase flowing through chamber 12 is determined by Henry's Law of Partial Pressure, in that gaseous species in the liquid mobile phase is caused to migrate through a gas-permeable membrane to a permeate side environment having a lower relative concentration or partial pressure of the target gaseous species than that found in the liquid mobile phase. For liquid chromatography applications, the critical gaseous species concentration in the liquid mobile phase is the maximum target gas species solute concentration sustainable in the mobile phase without outgassing. For example, methanol and water can each individually hold up to 38 percent of air without outgassing in any mixture combination of the two solvents. As such, the maximum pressure at permeate side 26 for degassing air from a methanol/water analyte may be calculated by the following relationship:

$$P_{Degas} = (0.38) \text{ (ambient atmospheric pressure)}$$

The ambient atmospheric pressure value must take into account known decreases in pressure introduced by the system. For example, flow restrictions between the mobile phase supply vessels and pump 14 must be deducted from ambient atmospheric pressure in order to calculate an accurate maximum pressure at permeate side 26 allowable in order to maintain the mobile phase with a gas concentration sufficiently low to prevent outgassing.

In some applications, however, such a pressure value calculated at a level only to prevent outgassing of the mobile phase is insufficient to adequately degas the mobile phase. As such, the gas pressure at permeate side 26 required to achieve desired degasification of the mobile phase is likely to be assessed for each set of operating conditions. In general, degassing rate is increased with decreased target gas partial pressure on permeate side 26 of chamber 12. To effectuate such an environment, permeate side 26 of chamber 12 is either evacuated to a relatively low total pressure, or a sweep fluid with little or no target gas concentration is passed through the chamber.

The equilibrium point pressure at permeate side 26 is calculated as the sum of the vapor pressures of each solvent component in the mobile phase. By operation of Dalton's Law, solvent vapor fills a void space to an extent at which its associated partial pressure meets the corresponding solvent vapor pressure, when such void space is exposed to the corresponding solvent. Such an arrangement is present in pervaporation control system 10, wherein permeate side 26 (void space) is available to be filled with solvent vapor up to the corresponding solvent vapor pressure of a solvent component disposed at retentate side 24. The Dalton's Law relationship holds that if permeate side 26 is maintained at a pressure equal to or greater than the sum of the vapor pressures of the respective solvents making up the mobile phase, pervaporation of the solvents will occur only to the extent that each solvent vapor fills permeate side 26 to a partial pressure equal to its corresponding vapor pressure, at which point further pervaporation ceases. Accordingly, Applicants have determined that pervaporation of mobile phase within chamber 12 can be limited by maintaining permeate side 26 at a total pressure equal to or greater than the sum of the vapor pressures of each mobile phase solvent component, while less than the outgassing pressure of the highest vapor pressure solvent component of the mobile phase.

As a further consequence of the Dalton's Law relationship, it has been determined by the Applicants that it is preferable to minimize the volume of permeate side 26 in chamber 12, such that the equilibrium point pressure described above is reached with as little solvent pervaporation as possible. Minimizing the void space defined by permeate side 26 provides a variety of other operational advantages, such as rapid pressure stabilization, low volume requirements, and the like.

The equilibrium point pressure required to cease pervaporation, however, may, in certain applications, be too high to provide adequate mobile phase degassing, and may even exceed the maximum pressure allowable to prevent outgassing effects in the mobile phase. Accordingly, for the purposes of this application, the equilibrium point pressure is typically the lesser of the sum of the solvent component vapor pressures, and the maximum permeate side pressure allowable to prevent outgassing effects in the particular mobile phase composition. In applications requiring higher degasification efficiency than that available at the equilibrium point pressure at permeate side 26, two or more permeate side pressure set point conditions may be programmed into control mechanism 16.

In certain embodiments, mobile phase degassing may be effectuated to a desired extent by modifying the separation membrane appropriately. For example, the membrane surface area may be increased by increasing its path length, the thickness of the membrane may be decreased, and/or the inside diameter of a membrane tube or the mean distance to the membrane wall of a flat membrane may be decreased. By so modifying the separation membrane, a desired degree of degasification of the mobile phase may be accomplished, even at permeate pressures exceeding the vapor pressures of the respective component materials being degassed. In such embodiments, therefore, the environment on the permeate side of the separation membrane need only be maintained at a pressure less than the outgassing pressure of the mobile phase.

As illustrated in the flow diagram of FIG. 4, control mechanism 16 may be programmed to calculate whether the desired level of mobile phase degasification requires a pressure at permeate side 26 that is lower than the equilibrium point pressure described above. If not, control mechanism 16 may simply assign a pressure set point at permeate side 26 to equal the equilibrium point pressure based on the particular mobile phase in use, and direct pump 14 to maintain such a pressure at all times.

If, however, the required pressure at permeate side 26 to reach a desired degree of degasification is indeed lower than the equilibrium point pressure, a first operating condition may be defined to maintain permeate side 26 at the desired degasification pressure, while a second operating condition may be defined to maintain permeate side 26 at the equilibrium point pressure. In such an arrangement, the first condition is activated and utilized to operate pump 14 at an appropriate rate to maintain the requisite permeate side pressure whenever control mechanism 16 detects at least a pre-defined critical flow rate of mobile phase through chamber 12. When such mobile phase flow rate is below such a designated critical flow rate in which pervaporation effects become problematic, control mechanism 16 is preferably programmed to institute the second condition by operating pump 14 at an appropriate rate to maintain only the equilibrium point pressure at permeate side 26 of chamber 12. It is contemplated by the Applicants, however, that a variety of conditions may be programmed into control mechanism 16, such that various pressures at permeate side 26 may be maintained at desired intervals, including pressures less than, equal to, or exceeding the sum of the vapor pressures of the corresponding solvent components of the mobile phase.

The multi-condition arrangement described above is thought to be particularly useful in relatively high throughput liquid degassing systems, wherein relatively low pressures must be maintained at permeate side 26 in order to achieve desired levels of mobile phase degasification during operation, while pervaporative effects may be minimized during shutdown or low-flow system conditions.

While the embodiment described above involves the use of a vacuum pump to at least partially evacuate chamber 12, it is contemplated by the present invention to achieve similar pervaporation control through the use of a sweep fluid at permeate side 26. To effectuate the pervaporation control of the present invention, the sweep fluid utilized at permeate side 26 preferably contains target gas and solvent vapor concentrations consistent with the desired level of gas transfer through membrane 22. For example, the sweep fluid concentration of the gaseous species targeted for removal from the analyte is preferably very low to promote gas transfer through Henry's Law across membrane 22 to permeate side 26. Moreover, the sweep fluid preferably contains sufficient concentrations of the solvent components of the mobile phase to exert partial pressures at permeate side 26 equal to or greater than the corresponding vapor pressures of the solvent components at retentate side 24. Through such an arrangement, degasification of the mobile phase is facilitated, while pervaporation of the mobile phase solvents is inhibited.

In embodiments utilizing sweep fluid control of pervaporation, control mechanism 16 is operably coupled to sweep fluid supply lines and respective flow valves thereof, such that control mechanism 16 may operably control the flow rate of one or more sweep fluids through permeate side 26 of chamber 12 based upon operator input and system conditions.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for controlling mobile phase pervaporation in a liquid degassing system, said method comprising:
    (a) providing a membrane disposed in a chamber, said membrane separating said chamber into a retentate side and a permeate side;
    (b) providing a control mechanism controllably coupled to a vacuum pump for selectively maintaining a designated environment on said permeate side of said chamber by processing measured and user-defined data and correspondingly operating said vacuum pump, said control mechanism including a data processor and a vacuum sensor for detecting pressure in said permeate side of said chamber, said vacuum sensor being communicatively coupled to said data processor to communicate sensed pressure in said chamber;
    (c) directing a mobile phase having two or more liquid component materials to said retentate side of said chamber;
    (d) inputting to said control mechanism:
        (i) identity data of said mobile phase component materials;
        (ii) any physical characteristics of said chamber necessary for said control mechanism to suitably operate said vacuum pump to control pervaporation of said mobile phase; and
        (iii) a maximum concentration threshold of a target gas within said mobile phase at a mobile phase outlet from said retentate side of said chamber;
    (e) obtaining mobile phase flow rate and temperature data;
    (f) based on said inputted and obtained data, said control mechanism being programmed to:
        (i) calculate respective vapor pressures of each of said liquid component materials of said mobile phase;
        (ii) calculate an outgassing pressure of said target gas within said mobile phase; and
        (iii) calculate a degassing pressure necessary to achieve a degassed target gas concentration that is less than or substantially equal to said maximum concentration threshold;
    (g) determining that said degassing pressure is less than a sum of said respective vapor pressures of said two or more liquid component materials; and
    (h) operating said control mechanism at selected ones of at least two alternative conditions, with a first condition being programmed to maintain a first total pressure on said permeate side that is substantially equal to or greater than said sum of said respective vapor pressures of said two or more liquid component materials, and a second condition being programmed to maintain a second total pressure on said permeate side that is substantially equal to said degassing pressure.

2. A method as in claim 1 wherein said control mechanism is operably coupled to a pump that is adapted to evacuate said permeate side of said chamber.

3. A method as in claim 1 wherein said first condition is programmed to further maintain said first total pressure at a value which is less than said outgassing pressure of said target gas within said mobile phase.

4. A method as in claim 3 wherein at least one of said first and second conditions are suitable for degassing said mobile phase.

* * * * *